United States Patent
Lamour et al.

(10) Patent No.: US 9,180,135 B2
(45) Date of Patent: Nov. 10, 2015

(54) MILIACIN AND SPHINGOLIPIDS AND/OR PHOSPHOLIPIDS COMPOSITION FOR HAIR AND SCALP CARE

(71) Applicant: HITEX, Vannes cedex (FR)

(72) Inventors: Irene Lamour, Vannes cedex (FR); Francois Laimay, Vannes cedex (FR); Emmanuelle Gaillard, Vannes cedex (FR)

(73) Assignee: ARCO S.A.S., Grasse (FR)

( * ) Notice: Subject to any disclaimer, the term of this patent is extended or adjusted under 35 U.S.C. 154(b) by 0 days.

(21) Appl. No.: 14/186,857

(22) Filed: Feb. 21, 2014

(65) Prior Publication Data
US 2014/0315864 A1 Oct. 23, 2014

(30) Foreign Application Priority Data

Apr. 26, 2013 (FR) .................... 13 53864

(51) Int. Cl.
| | |
|---|---|
| *A61F 13/02* | (2006.01) |
| *A61K 31/66* | (2006.01) |
| *A61K 31/075* | (2006.01) |
| *A61K 31/164* | (2006.01) |
| *A61L 15/44* | (2006.01) |
| *A61K 8/33* | (2006.01) |
| *A61Q 5/00* | (2006.01) |
| *A61K 8/55* | (2006.01) |
| *A61Q 5/02* | (2006.01) |
| *A61Q 5/12* | (2006.01) |
| *A61Q 7/00* | (2006.01) |
| *A61K 8/68* | (2006.01) |
| *A61K 8/97* | (2006.01) |
| *A61K 8/14* | (2006.01) |

(52) U.S. Cl.
CPC . *A61K 31/66* (2013.01); *A61K 8/14* (2013.01); *A61K 8/33* (2013.01); *A61K 8/553* (2013.01); *A61K 8/68* (2013.01); *A61K 8/97* (2013.01); *A61K 31/075* (2013.01); *A61K 31/164* (2013.01); *A61L 15/44* (2013.01); *A61Q 5/00* (2013.01); *A61Q 5/02* (2013.01); *A61Q 5/12* (2013.01); *A61Q 7/00* (2013.01); *A23V 2200/316* (2013.01); *A61K 2800/92* (2013.01)

(58) Field of Classification Search
CPC ... A61Q 7/00; A61Q 19/00; A23V 2200/316; A61L 15/44
See application file for complete search history.

(56) References Cited

FOREIGN PATENT DOCUMENTS

FR 2785806 5/2000

OTHER PUBLICATIONS

Obrigkeit et al, Xenobiotics in Vitro: The Influence of L-Cystine, Pantothenat, and Miliacin on Metabolic and Proliferative Cpacity of Keratinocytes, Cutan Ocul Toxicol, 2006, 25(1), 13-22.*
"Hlrsatia by Zwicky AG" Product review: Hirsana Capsules for Skin, Hair and Nails by Nicki Zevola, Jul. 12, 2009 viewed at (https://www.futurederm.com/product-review-hirsana-capsules-for-skin-half-ard-nails/).
"Lipowheat by HITEX", Hitex, Aug. 8, 2011.
Henning, "Millet Oil for Skin and Hair Care", SOFW Journal, 131, 4-2005, pp. 1-8.

* cited by examiner

*Primary Examiner* — Carlos Azpuru
(74) *Attorney, Agent, or Firm* — Kramer Amado, P.C.

(57) ABSTRACT

The present disclosure relates to a cosmetic or dietary composition for combating human or animal hair loss and/or promoting hair growth and/or regrowth and/or enhancing the beauty thereof (shine, softness, strength) and/or enhancing scalp comfort, comprising at least miliacin in a proportion greater than 0.1% by mass with respect to the total mass of the composition and polar lipids in a proportion greater than 0.1% by mass with respect to the total mass of the composition, including sphingolipids, particularly ceramides and/or glycosylceramides, and/or phospholipids in a proportion greater than 0.1% by mass with respect to the total mass of the composition. The present disclosure further relates to the use of such a composition, and the method for preparing such a composition.

23 Claims, No Drawings

MILIACIN AND SPHINGOLIPIDS AND/OR PHOSPHOLIPIDS COMPOSITION FOR HAIR AND SCALP CARE

FIELD OF THE DISCLOSURE

The present disclosure relates to the field of the cosmetic care of scalp and keratin materials, particularly human hair. The disclosed formulation is also applied for the cosmetic treatment of animal hair, particularly pet and domestic animals.

In particular, the disclosure relates to a composition for oral administration or for skin application, comprising an association of active substances for combating hair loss and/or promoting hair growth and/or regrowth and/or enhancing the beauty thereof (shine, softness, strength) and/or enhancing scalp comfort or, in animals, combating excessive hair loss and/or promoting hair growth and/or enhancing the beauty thereof.

The disclosure further relates to the use of such a composition, and the method for preparing such a composition.

BACKGROUND

The hair consists of a shaft, which is the visible part, a hair bulb situated 3 or 4 mm under the scalp surface and a dermal papilla. The shaft consists of 95% keratin, water, fatty acids, melanin and a small quantity of iron and zinc.

The shaft is surrounded by two sheaths: the inner root sheath necessary for hair growth and the outer root sheath having a similar composition to that of the epidermis. They determine the definitive shape of the hair. The outer root sheath particularly hosts the stem cells from which the hair follicle is cyclically regenerated.

On the entire surface thereof, the fibre is protected by a thin layer referred to as the cuticle. It is formed from overlapping colourless cells called scales. Cohesion between these scales is provided by a cement rich in lipids and in ceramides in particular.

The bulb consists of actively dividing keratinocytes to form the hair shaft and the inner and outer root sheaths.

The dermal papilla at the base of the bulb enables hair irrigation and oxygenation and cellular waste disposal. It consists of fibroblasts secreting an important extracellular matrix. Highly vascularised, it is involved in hair nutrition and regulation functions. The papilla can be considered to be the biological motor of the hair.

Hair Life Cycle

Individual hair emerge, grow and fall out according to the independent hair life cycle comprising the following phases.

The anagen phase is the hair growth phase, during which the hair grows from the bulb. Hair matrix cells undergo significant division to form the hair shaft and the inner and outer root sheaths. In the anagen phase, the hair matrix is the site of intense cellular proliferation. The hair shaft is then keratinised. Simultaneously, the hair follicle grows in the deep layers of the skin to nourish the hair. This is the longest period of the hair life cycle, lasting 2 to 5 years on average. The majority of hair is in the anagen phase.

The catagen phase is a resting phase during which the hair stops changing. This phase last approximately 3 weeks.

Finally, during the telogen phase, the hair no longer grows, but remains attached to the hair follicle. At the end of this phase, the old hair falls out, leaving its place for a new follicle in the anagen phase, and the hair life cycle is resumed. During this phase, there is little or no cellular proliferation, and no further hair shaft growth is observed.

If the hair life cycle is normal, the percentage of hair in the anagen phase is between 85 and 90% of all hair, the catagen phase applies to approximately 1% of hair and approximately 10 to 15% of hair is in the telogen phase.

However, during a man or woman's lifetime, for various reasons, the hair life cycle may be subject to abnormal changes. The causes of such changes may particularly be the change of season, fatigue, stress, hormonal imbalance, hair treatment, medication having an effect on hair, pollution or ageing. In this case, the percentage of hair in the anagen phase may fall below 80% of all hair and the hair in the telogen phase may be in a proportion greater than 20% of all hair. The hair loss becomes excessive. This abnormal hair loss is accompanied by weakening of the hair structure.

Similarly, some animals with hair, such as pets, sometimes undergo short- or long-term abnormally excessive hair loss.

Prior Art Solutions

To remedy all or part of this imbalanced hair life cycle problem giving rise to abnormally significant hair loss and weakening of the hair, some medicinal products, cosmetic products or dietary supplements are known.

In particular, active substances of medicinal products such as minoxidil and finasteride (or propecia) are known. These active substances are genuinely effective but involve the drawback of being chemical products, potentially, as for any synthetic molecules, producing adverse side effects in the patient such as irritation or thickening of body hair, among others. Furthermore, finasteride is not recommended for women.

Moreover, dietary supplements based on vitamins and minerals are known, with a claimed effect on the beauty of skin appendages and skin, without particularly targeting an "antihair loss" treatment. However, these vitamins and minerals are readily available as part of a varied and balanced diet.

Further dietary supplements containing plant extracts optionally associated with vitamins and minerals exist. They are mostly used traditionally, but without clinical studies proving the efficacy thereof. Examples include pumpkin seed oil, brewer's yeast, green tea, soy isoflavones.

Further dietary supplements only apply to excessive hair loss associated with hormonal imbalance, particularly androgenetic alopecia. For example, this is the case of dietary supplements based on Saw-palmetto. These dietary supplements are essentially intended for men.

A further known dietary supplement, marketed under the brand Priorin® by Bayer, promotes hair growth by supplying the cells with essential nutrients. It contains a whole golden millet and wheat germ oil extract, associated with cystine and an essential vitamin for hair, calcium panthothenate. Wheat germ oil consists of fatty acids such as linoleic acid and vitamin E.

A further dietary supplement marketed under the trade name Hirsana® by Zwicky AG is based on millet oil containing miliacin associated with vitamins and minerals to help stop hair loss and strengthen hair and nails.

SUMMARY

The present disclosure provides a composition, used as a cosmetic or dietary supplement, which is genuinely effective and targeted for combating human or animal hair loss and/or promoting hair growth and/or regrowth and/or enhancing the beauty thereof (shine, softness, strength) and/or enhancing scalp comfort.

A further aim of the present disclosure is that of providing such a composition including only natural plant extracts.

A further aim of the present disclosure is that of providing such a composition which does not cause adverse side effects and does not modify the hormonal balance of the subject or animal concerned.

Various embodiments disclosed herein relate to a cosmetic or dietary composition, comprising from 0.01% to 10% by weight miliacin, based on the total weight of said cosmetic or dietary composition; and from 0.01% to 5% by weight of at least one sphingolipid, based on the total weight of said cosmetic or dietary composition. Certain embodiments relate to a cosmetic or dietary composition, comprising from 0.01% to 10% by weight miliacin, from 0.01% to 5% by weight of a sphingolipid, based on the total weight of said cosmetic or dietary composition, and from 0% to 5% of phospholipids, based on the total weight of said cosmetic or dietary composition. In some embodiments, the composition comprises from 0.01% to 5% of phospholipids, based on the total weight of said cosmetic or dietary composition. In various embodiments disclosed herein, the composition may contain from 0.1% to 2% by weight of the miliacin. The composition may additionally comprise a pharmaceutically acceptable medium or excipient; or a food-grade acceptable medium. A suitable pharmaceutically acceptable medium may comprise water, an oil, or a fatty acid, such as linoleic acid. Suitable excipients include, as examples, maltodextrins, lactose, starches, modified starches, microcrystalline cellulose, silica, and alumina.

In various embodiments disclosed herein, the composition may contain greater than 0.1% by weight of the sphingolipids. The sphingolipids in the cosmetic or dietary composition comprises at least one ceramide, at least one glycosylceramide, or a mixture thereof. In various embodiments, the composition may contain from 0.1% to 1% by weight of at least one ceramide, at least one glycosylceramide, or a mixture thereof. The composition may additionally contain between 0.01% and 5% of at least one phospholipid, from 0.3% to 1.5% of at least one phospholipid, or from 0.5% to 1.5% of at least one phospholipid.

In various embodiments disclosed herein, the composition may comprise a cosmetic or dietary composition, comprising a combination of miliacin and sphingolipids. The composition comprises from 20% to 90% by weight miliacin, from 50% to 85% miliacin, or from 60% to 85% miliacin, based on the combined weight of miliacin and sphingolipid in the composition. The composition may further comprise an optional phospholipid; and a pharmaceutically acceptable medium.

Various embodiments disclosed herein relate to a cosmetic or dietary composition, comprising millet oil, a polar organic solvent extract of wheat, and a pharmaceutically acceptable medium. The millet oil is present in an amount effective to provide a cosmetic or dietary composition containing from 0.01% to 10% by weight miliacin, or from 0.1% to 2% by weight miliacin, based on the total weight of said cosmetic or dietary composition. The polar organic solvent extract of wheat comprises a sphingolipid; and is present in the cosmetic or dietary composition effective to provide the composition with between 0.01% and 5% by weight sphingolipid, based on the total weight of the composition.

Various embodiments disclosed herein relate to a composition prepared by obtaining a millet oil comprising miliacin; obtaining a polar organic solvent extract of wheat, wherein said polar organic solvent extract of wheat comprises a sphingolipid; and mixing the millet oil and the wheat extract. In various embodiments, the step of obtaining a millet oil comprises extraction of millet seeds with a polar or nonpolar solvent selected from the group consisting of supercritical $CO_2$, supercritical propane, hexane, ethanol, and isopropanol. The step of obtaining a polar organic solvent extract of wheat may comprise extraction of wheat with ethanol.

Various embodiments disclosed herein relate to a composition prepared by mixing a millet oil and a polar organic solvent extract of wheat. In various embodiments, the mixing step comprises injecting a polar organic solvent extract of wheat into a millet oil extraction circuit during extraction of millet seeds. The mixing step may comprise injecting a polar organic solvent extract of wheat into a millet oil extraction circuit during extraction of millet seeds during extraction of millet seeds with an oxygen-free, supercritical medium, such as supercritical $CO_2$.

Various embodiments disclosed herein relate to a method of reducing hair loss or promoting hair growth in a patient in need thereof, by administering an effective amount of a composition comprising from 0.01% to 10% by weight miliacin and from 0.01% to 5% by weight of a sphingolipid to the patient. The composition may be administered topically or orally.

DESCRIPTION OF VARIOUS EMBODIMENTS

The present disclosure achieves all or part of the above-mentioned aims by means of cosmetic or dietary composition for combating human or animal hair loss and/or promoting hair growth and/or regrowth and/or enhancing the beauty thereof (shine, softness, strength) and/or enhancing scalp comfort, comprising at least miliacin in a proportion greater than 0.01%, particularly 1.0% by mass with respect to the total mass of the composition and polar lipids in a proportion greater than 0.1% by mass with respect to the total mass of the composition, including sphingolipids, particularly ceramides and/or glycosylceramides, and/or phospholipids in a proportion greater than 0.1% by mass with respect to the total mass of the composition.

The present disclosure provides a particularly effective composition based on natural products, having a targeted activity for combating hair loss and promoting hair growth.

Surprisingly and unexpectedly, the inventors discovered that the composition associating miliacin at a lower dose with polar lipids has a largely superior activity to that of miliacin alone, which was previously known. Indeed, miliacin is known to accelerate cell division at the bulb and activate the cellular metabolism.

In the composition according to the present disclosure, associating miliacin and polar lipids in the same composition makes it possible, in the presence of water as is the case in the intestinal environment, to form structures capable of encapsulating miliacin. The liposomes formed enhance the bioavailability of miliacin by promoting intestinal passage, as previously described for other molecules (curcumin, naringenin).

Advantageously, the miliacin and polar lipids are of plant origin.

Miliacin

Miliacin is a triterpenoid only currently found in millet, *Panicum miliaceum*. Miliacin was first studied for the healing properties thereof and activity thereof on cellular proliferation. It has been used for some time in dietary supplements intended for hair care and health, as mentioned above.

Miliacin is advantageously present in the composition according to the present disclosure in a proportion by mass between 0.1% and 10%, particularly in a proportion greater than 0.5%, for example less than 2%, particularly 1%, with respect to the total mass of the composition.

The miliacin is contained in a millet oil, for example obtained using supercritical $CO_2$.

Such an oil is obtained by grinding whole or hulled *Panicum miliaceum* millet seeds to obtain millet meal. Extraction is then performed, for example using supercritical $CO_2$. The millet extract obtained is then vacuum-dried and stabilised with a rosemary extract to prevent any risk of oxidation.

The composition of this millet extract is preferentially as follows: 85 to 99% triglycerides (including linoleic acid, oleic acid and palmitic acid in particular), 0.5 to 2% sterols (including beta-sitosterol, delta-7-stigmasterol and other sterols), and 0.1 to 2% miliacin.

Polar Lipids

Polar lipids are a separate lipid class since they have a hydrophilic part enabling them to play a predominant role at interfaces, in living organisms or in dispersed systems. In particular, they are the main constituents of biological membranes.

Sphingolipids, particularly ceramides and glycosylceramides, play major biological roles in the very structure of the epidermis, for example. In this region, the corneocytes are separated by intercellular spaces, lined with multi-lamellar intercorneocyte cement. This intercorneocyte cement mainly consists of ceramides and glycosylceramides (35 to 40%) and limits water loss while ensuring cellular cohesion in the epidermis. Recent studies have demonstrated that a portion of the ceramides and glycosylceramides ingested are found in the skin. Clinical studies have demonstrated the moisturising activity of ceramides and glycosylceramides taken orally and an improvement in the clinical signs associated with dry skin, such as redness, flakiness or itchiness.

Ceramides are also found in the hair cuticle where they ensure intercellular cohesion and protect hair from the entry of undesirable compounds. They also have a structural role and provide the mechanical properties of the hair.

Phospholipids are key constituents of the biological cell membrane and represent approximately 55% of membrane lipids. They have the ability to organise themselves into a dual layer, with the hydrophilic heads thereof pointing outwards and the hydrophobic chains thereof pointing towards the inside of the membrane.

A further property of polar lipids, and phospholipids in particular, which is of particular interest in the present disclosure, relates to the abilities thereof to act as a vector or substrate, increasing the bioavailability of the active compounds. Indeed, phospholipids are recognised and used for the ability thereof to form vesicles. These vesicles may enhance the bioavailability of some active substances, facilitating intestinal passage.

According to one preferred embodiment, the proportion of polar lipids is greater than 0.5% with respect to the total mass of the composition.

Advantageously, the polar lipids comprise sphingolipids, particularly ceramides and/or glycosylceramides. In this case, the proportion by mass of ceramides and/or glycosylceramides is advantageously between 0.01% and 5%, particularly between 0.1% and 1% with respect to the total mass of the composition, particularly greater than 0.1% or 0.2% with respect to the total mass of the composition.

The polar lipids may also comprise phospholipids. In this case, the proportion by mass of phospholipids is advantageously between 0.01% and 5%, particularly between 0.3% and 1.5% with respect to the total mass of the composition, for example greater than 0.5%, or 0.8% with respect to the total mass of the composition.

The polar lipids, particularly sphingolipids, such as ceramides and/or glycosylceramides, and/or phospholipids, may particularly be contained in a plant-based lipid extract, in extracts of plants such as konjac, or in extracts of grains or legumes rich in polar lipids, such as corn, rice, wheat or soy, or in dairy products rich in polar lipids.

In the case of wheat extract, it consists for example of a vegetable oil or a lipid powder suitable for being obtained according to the method described in the patent FR 2 785 806, the content whereof is incorporated herein as a reference. The extraction method described in the patent FR 2 785 806 particularly uses ethanol as a solvent.

In particular, the wheat extract may consist of that marketed under the name Lipowheat® by HITEX, the holder of the present application.

The method for preparing Lipowheat® may comprise the step for harvesting *Triticum aestivum/vulgare* wheat grains, followed by leaching the ground grains to obtain gluten on one side and starch on the other, and, by means of ethanol extraction of the wheat gluten, obtaining Lipowheat® oil and after a second extraction using acetone, obtaining Lipowheat® powder.

Formation of Vesicles in the Presence of Polar Lipids, Miliacin and Water

The optical microscopic examinations of a mixture containing polar lipids supplied by Lipowheat®, miliacin in crystal form, and water, clearly indicate vesicle formation. These relatively rigid structures are between 5 and 25 μm in diameter.

This system is only observed in the presence of miliacin, which plays a key role at the interface of liposomes which stiffen to form actual capsules.

The liposomes formed enhance the bioavailability of miliacin by promoting intestinal passage, as previously described for other molecules (curcumin, naringenin).

Average Composition of Formula According to the Present Disclosure

Three forms of the composition according to the present disclosure are available:

an oily form named KERANAT a water-soluble powder form (1) named KERANAT WS POWDER a water-dispersible powder form (2) named KERANAT POWDER Oil Form: KERANAT

|  | Average content | Preferential content |
| --- | --- | --- |
| Linoleic acid | 30-70% | 50-65% |
| Miliacin | 0.01-10% | 0.1-2% |
| Phospholipids | 0.01-5% | 0.30-1.5% |
| Ceramides and Glycosylceramides | 0.01-5% | 0.1-1% |
| Other fatty acids | 10-40% | 15-30% |
| Other lipids | 0.01-5% | 0.5-3% |

Powder Form 1: KERANAT WS POWDER

|  | Average content | Preferential content |
| --- | --- | --- |
| KERANAT | 10.00%-50.00% | 20.00%-30.00% |
| Maltodextrins | 20.00%-60.00% | 40.00%-50.00% |
| Modified starch | 10.00%-50.00% | 30.00%-40.00% |

Powder Form 2: KERANAT POWDER

|  | Average content | Preferential content |
|---|---|---|
| KERANAT | 10.00%-50.00% | 20.00%-30.00% |
| Baobab pulp | 50.00%-90.00% | 70.00%-80.00% |
| Silica | 0.00%-5.00% | 0.00%-2.00% |

Other Constituents

The composition according to the present disclosure may further be used in the field of nutrition, as a dietary supplement or functional food in any dosage form: tablets, hard capsules, soft capsules, drinks or other.

The composition according to the present disclosure may incorporate dietary supplement formulas where it may be associated with compounds known to those skilled in the art and thus comprise sulphur amino acids, vitamins, particularly B vitamins, minerals, particularly copper, zinc or selenium, or a plant extract.

The composition according to the present disclosure may also be used in topical form in any dosage form: oil, water-based gel, lipid-based gel, oil-in-water emulsion, water-in-oil emulsion, foaming and cleansing gel, soap, patch or lotion or any other topical dosage concept known to those skilled in the art. The composition according to the present disclosure may incorporate oral and/or topical cosmetic formulas containing lipids, gelling or thickening polymers, surfactants and emulsifiers, water-soluble or fat-soluble active substances, or extracts of other raw materials, used routinely in cosmetics and known to those skilled in the art.

Method for Preparing a Composition According to the Present Disclosure

A further object of the present disclosure, in combination with the above, is that of a method for preparing the composition as defined above, comprising the following steps:
 obtaining a millet oil comprising miliacin by extraction,
 obtaining an oily ingredient comprising sphingolipids, particularly glycosylceramides and/or ceramides and/or phospholipids by means of ethanol extraction, and
 mixing the millet oil and oily ingredient, particularly at atmospheric pressure or under supercritical conditions during the extraction of the millet.

The extraction for obtaining millet oil may for example be chosen from the group of the following techniques: supercritical fluid extraction, particularly with supercritical $CO_2$ or supercritical propane, and solvent extraction, particularly with hexane, ethanol or isopropanol.

Advantageously, the millet oil is extracted using the supercritical $CO_2$ extraction technique. Extraction using this technique has a good yield and the extract obtained from this technique is of high quality.

The lipid extraction for obtaining the oily ingredient comprising sphingolipids, particularly glycosylceramides and/or ceramides, and/or phospholipids may be for example a solvent extraction, particularly with ethanol.

The mixing of the millet oil and the oily ingredient may, according to a first embodiment, be implemented at the end of the method by mixing after obtaining each of the ingredients, at atmospheric pressure in particular.

Alternatively, according to a second, preferential, embodiment, the mixing of the millet oil and oily ingredient may be implemented by adding, particularly by injection, the oily ingredient into a millet oil extraction circuit, during extraction, particularly during supercritical $CO_2$ extraction. The mixing step may particularly be derived from the technique described in the method according to the patent FR 99 13241.

The oily ingredient comprising polar lipids is added in the millet oil extraction circuit in an oxygen-free, supercritical medium.

The composition prepared in an oxygen-free medium is not subject to oxidation and is more stable. The implementation of this step of the method thus makes it possible to obtain a more homogeneous and more stable composition.

Use of a Composition According to the Present Disclosure

A further object of the present disclosure, in combination with the above, is that of using a composition comprising at least miliacin in a proportion greater than 0.1% by mass with respect to the total mass of the composition and polar lipids, particularly sphingolipids, such as ceramides and/or glycosylceramides, and/or phospholipids, in a proportion greater than 0.1% by mass with respect to the total mass of the composition, for combating human or animal hair loss and/or promoting hair growth and/or regrowth and/or enhancing the beauty thereof (shine, softness, strength) and/or enhancing scalp comfort.

Tests

The disclosed subject matter, along with the advantages offered, will be understood more clearly using the examples of embodiments thereof described hereinafter, conducted in vitro and in vivo.

Test 1: In Vitro Test

Purpose of In Vitro Test

This test consists of studying the cellular proliferation of root cells (keratinocytes). Indeed, as mentioned above, cellular proliferation at the hair bulb matrix promotes hair growth.

The purpose of this test is to verify the data described in the scientific literature for miliacin and evaluate the benefit of an association between miliacin and polar lipids.

Compositions Studied:
 Composition A: 1.7 µg/ml of miliacin
 Composition B: 150 µg/ml of the composition disclosed herein, Keranat, comprising:
  1.7 µg/ml of miliacin (1.1% of mixture)
  0.30 µg/ml of glycosylceramides and ceramides (0.21% of mixture)
  1.2 µg/ml of phospholipids (0.8% of mixture)

Methodology

Human scalp fragments were obtained in plastic surgery from twelve different donors from the occipital area prior to hair implantation. They were deposited in inserts, in turn placed in culture wells. Culture medium specifically suitable for maintaining survival conditions (antibiotic, foetal calf serum (FCS)) was added to the bottom of the wells, running a passage by slow diffusion between the two compartments via a 3 µm thick porous membrane.

The composition is added in dilution at a predetermined dose, in the culture medium to promote contact with the hair bulbs.

Three series of scalps were compared during two successive tests:
 one control scalp;
 one scalp whereon composition A comprising miliacin alone was applied;
 one scalp whereon composition B according to the present disclosure, comprising miliacin and polar lipids, including ceramides, glycosylceramides and phospholipids, was applied.

The cultures were stopped on D4 (fourth day) and the scalp fragments were fixed in formol to enable the immuno-histochemical analyses.

Method for Analysing the Results

The root proliferation was analysed by means of immuno-histochemistry using an anti-Ki67 antibody marker of phase M, S, G1 and G2 cells in the cell cycle (mouse monoclonal antibody, MIB1 clone, diluted to 1:300, marketed by Dako). The immunodetection was carried out using an amplified four-layer indirect immunoperoxidase technique (CsA kit, marketed by Dako) and stained red with AEC (3-amino-9-ethylcarbazole).

On each bulb, the number of positive cells is counted with respect to a total of approximately 100 cells. For each scalp, the analysis is performed on approximately 8 different donors.

Results Obtained

The results obtained are as follows:

| | Study area | Results (% of proliferating cells compared to control) |
|---|---|---|
| Composition A Miliacin alone | bulb | +92% |
| Composition B Miliacin and polar lipids | bulb | +138% |

The number of proliferating cells is 92% greater in the hair bulbs in contact with millet oil alone.

The number of proliferating cells is 138% greater in the hair bulbs in contact with the composition according to the present disclosure.

The gain in performance, with the composition according to the disclosure, associating miliacin with polar lipids, is thus approximately 50%. Surprisingly and unexpectedly, the enhancement of the efficacy performance, on cellular proliferation in the region of the bulb, of miliacin by adding polar lipids, is very significant and unequivocal.

Associating active agents such as polar lipids including ceramides, glycosylceramides and phospholipids, with miliacin, in the composition according to the disclosure, thus, unexpectedly, enables enhanced action on cellular proliferation in the region of the bulb, compared to miliacin alone.

Test 2: In Vivo Tests

Purpose of In Vivo Tests

These tests consist of demonstrating, firstly, the anti-hair loss efficacy of miliacin alone, and, secondly, the equivalent efficacy of a lower dose of miliacin associated with polar lipids in an association according to the disclosure.

Indeed, since miliacin is a rare lipid, the inventors sought to check whether, by reducing the amount of miliacin in the composition while adding polar lipids, the effect of the composition would have the same intensity.

First Clinical Study:

Purpose: evaluate the anti-hair loss efficacy of millet oil extracted with supercritical $CO_2$, with a standardised miliacin content, in the form of a soft capsule providing 350 mg per day of the formula, i.e. 3.5 to 4.0 mg/day of miliacin.

A first clinical study was conducted on 60 female volunteers, having an average age of 37 years. The aim of this study is that of demonstrating the efficacy of a product comprising miliacin, as the sole active substance, on hair loss.

Composition

The composition tested comprises between 3.5 and 4 mg of miliacin, approximately 200 to 250 mg of linoleic acid and 50 to 100 mg of other fatty acids.

| Molecules | Content in test composition |
|---|---|
| Linoleic acid | 200-250 mg |
| Miliacin | 3.5-4.0 mg |
| Other fatty acids | 50-100 mg |
| Tested daily dose | 350 mg |

Methodology

The study was conducted on a double-blind, placebo-controlled and randomised basis. The tests took place at a time t0 and at a time t12, 12 weeks after t0. The parameters observed during the study are the number of hairs, the percentage of hair in the anagen phase and telogen phase, hair strength and general hair appearance.

The method used to determine the percentage of hair in the telogen and anagen phase is the Trichogram with Trichoscan®.

Significant initial results were obtained after three months of use and a daily dose of 350 mg of product.

Results

The results show that the composition based on miliacin reduces the percentage of hair in the telogen phase by approximately 8%, decreasing the number of hairs in the telogen phase from approximately 21.5% to 19.8%.

The placebo is stable, with the number of hairs in the telogen phase not decreasing (very slight increase of 0.03%).

The difference between the composition based on miliacin and the placebo is significant after three months of use.

Second Clinical Study:

Purpose: evaluate the anti-hair loss efficacy of an original association of millet oil extracted with supercritical $CO_2$, with a standardised miliacin and polar lipid content, in the form of a soft capsule providing 300 mg per day of the formula, i.e. 3.0 to 3.3 mg/day of miliacin. The purpose of this study is to demonstrate the equivalent efficacy of a lower dose of miliacin when associated with polar lipids.

A second clinical study is conducted on 65 women with millet oil associated with polar lipids including glycosylceramides, ceramides and phospholipids, corresponding to a composition according to the present disclosure.

Test Composition

The composition under test comprises between 3.0 and 3.3 mg of miliacin and between 0.5 and 0.8 mg of glycosylceramides and ceramides, between 2 and 4 mg of phospholipids, approximately 150 to 200 mg of linoleic acid and 50 to 100 mg of other fatty acids.

| Molecules | Content in test composition |
|---|---|
| Linoleic acid | 150-200 mg |
| Miliacin | 3.0-3.3 mg |
| Glycosylceramides and ceramides | 0.5-0.8 mg |
| Phospholipids | 2.0-4.0 mg |
| Other fatty acids | 50-100 mg |
| Tested daily dose | 300 mg |

Methodology

This study consisted of a randomised, double-blind placebo-controlled study for 12 weeks. The study conditions were double-blind and randomised, and tests took place at a time t0, at a time t6 and at a time t12, 12 weeks after t0.

The parameters observed in the study are the number of hairs, the percentage of hair in the anagen phase and telogen phase and the general appearance of the hair and scalp. The method used to determine the percentage of hair in the telogen and anagen phase is the Trichogram.

Results

The results obtained are not only, as expected, at least equivalent to those of the first clinical study, but are furthermore largely superior to those of the first clinical study, with an improvement of more than 500% after three months of use and a daily dose of 300 mg of composition, whereas the dose intake is reduced by approximately 25% with respect to the first clinical study.

Indeed, a reduction of approximately 50% in the percentage of hair in the telogen phase was observed after three months of use of the composition according to the present disclosure. The composition slowed down hair loss significantly and in a very superior manner with respect to the previous study.

The results obtained following these two clinical studies prove, unequivocally and in surprising proportions, the singularity of the association of miliacin with polar lipids. The synergistic action between the two ingredients is unexpected and the efficacy demonstrated indicates anti-hair loss activity which is well above expectations.

The 300 mg dose of the composition according to the present disclosure, providing approximately 3 mg of miliacin, is 6 times more effective for reducing the percentage hair in the telogen phase, than miliacin alone at 4 mg in a vegetable oil at a dose of 350 mg.

Completely unexpectedly, by reducing the daily dose of miliacin by 25% and by associating, in an original manner, miliacin with polar lipids, the performance is multiplied by 6, which is considerable and unexpected.

|  | Product under study | Daily dose | RESULT |
| --- | --- | --- | --- |
| STUDY 1 | Millet oil containing 1% miliacin | 350 mg 3.5 to 4.0 mg of miliacin | Reduction of percentage of hair in telogen phase by 8% |
| STUDY 2 | Composition according to the present disclosure containing millet oil with 1% miliacin and polar lipids | 300 mg 3.0 to 3.3 mg of miliacin + polar lipids | Reduction of percentage of hair in telogen phase by 50% |

Moreover, 91% of women taking the composition experienced a reduction in hair loss. A 73% reduction in the presence of dandruff and a 75% reduction in dry scalp were also observed.

This second clinical study provides unprecedented proof of the benefit of an association, as described in this patent, between miliacin and polar lipids for increasing the anti-hair loss properties of miliacin.

EXAMPLES

Dietary Supplement Formulas

Dietary Supplement A

This consists of a dietary supplement in the form of one or two soft capsules per day containing the following ingredients:

| Ingredients | Content in capsule, in mg |
| --- | --- |
| Composition according to the present disclosure KERANAT | 300 mg, providing approx. 3.0 to 3.3 mg of miliacin and 0.5 mg to 0.8 mg of glycosylceramides and ceramides and 2 to 4 mg of phospholipids. |
| Zinc | 10 mg = 100% of RDA |
| Vitamin B6 | 1.4 mg = 100% of RDA |
| Vitamin B8 | 50 µg = 100% of RDA |

Dietary Supplement B

This consists of a dietary supplement in the form of two soft capsules per day containing the following ingredients:

| Ingredients | Content in capsule, in mg |
| --- | --- |
| Composition according to the present disclosure KERANAT | 300 mg, providing approx. 3.0 to 3.3 mg of miliacin and 0.5 mg to 0.8 mg of glycosylceramides and ceramides and 2 to 4 mg of phospholipids. |
| Pumpkin seed oil | 500 mg |
| Cystine | 20 mg |
| Vitamin B5 | 10 mg = 100% of RDA |

Dietary Supplement C

This consists of a dietary supplement in the form of one or two soft capsules per day containing the following ingredients:

| Ingredients | Content in capsule, in mg |
| --- | --- |
| Composition according to the present disclosure KERANAT | 300 mg, providing approx. 3.0 to 3.3 mg of miliacin and 0.5 mg to 0.8 mg of glycosylceramides and ceramides and 2 to 4 mg of phospholipids. |
| Keratin | 100 mg |
| Zinc | 10 mg = 100% of RDA |
| Vitamin B6 | 1.4 mg = 100% of RDA |

Dietary Supplement D

This consists of a dietary supplement in the form of one stick per day containing the following ingredients:

| Ingredients | Content in sachet or stick, in mg |
| --- | --- |
| KERANAT WS POWDER | 1.5 g providing approx. 3.0 to 3.3 mg of miliacin and 0.5 mg to 0.8 mg of glycosylceramides and ceramides and 2 to 4 mg of phospholipids. |
| Keratin | 500 mg |
| Cystine | 20 mg |
| Zinc | 10 mg = 100% of RDA |
| Vitamin B6 | 1.4 mg = 100% of RDA |
| Vitamin B5 | 10 mg = 100% of RDA |
| Vitamin B8 | 50 µg = 100% of RDA |

Dietary Supplement E

This consists of a dietary supplement in the form of one stick or sachet per day containing the following ingredients:

| Ingredients | Content in sachet or stick, in mg |
| --- | --- |
| KERANAT POWDER | 1.5 g providing approx. 3.0 to 3.3 mg of miliacin and 0.5 mg to 0.8 mg of glycosylceramides and ceramides and 2 to 4 mg of phospholipids. |
| Green tea extract | 300 mg |
| Taurine | 150 mg |
| Cystine | 150 mg |
| Zinc | 10 mg = 100% of RDA |
| Vitamin B6 | 1.4 mg = 100% of RDA |

-continued

| Ingredients | Content in sachet or stick, in mg |
|---|---|
| Vitamin B5 | 10 mg = 100% of RDA |
| Vitamin B8 | 50 μg = 100% of RDA |

Cosmetic Formulas

In humans, the skin covers the entire body for a total surface area of approximately 2 m2, and weighs approximately 5 kg. The scalp covers approximately 600 cm2 i.e. approximately $1/33^{rd}$ of the skin on the body, weighing approximately 0.15 kg. Given that the average weight of a woman is approximately 63 kg, the mass of the scalp thus represents approximately $1/420^{th}$ of body mass.

It was demonstrated that 300 mg/day of the composition according to the present disclosure had, on a woman of average weight, an effect on hair loss, growth and/or regrowth and/or on enhanced beauty and/or enhanced scalp comfort.

The mass of the scalp is 420 times less than the total body mass. If the same factor is used to determine the equivalent dose to the effective oral dose, i.e. 300 mg, this gives 0.7 mg of the composition according to the present disclosure, per day and per application dose (in the case of a single daily application).

Applying a lotion for example in spray form should thus dispense this amount in one 1 ml of product, this quantity corresponding to an average application. However, 1 ml of aqueous solution weighs approximately 1 g; 0.7 mg is thus equivalent to 0.07% M/M of active substance in the finished product.

Loss caused by transdermal passage and enzyme attacks on the skin surface is generally anticipated by those skilled in the art. By increasing the concentration by a factor of 10, the concentration of product according to the present disclosure is standardised at 0.7% M/M of a cosmetic formula.

Formula 1—Shampoo for Everyday Use

| Supplier | Ingredient | Active substance | % |
|---|---|---|---|
| MASSO | Sulfetal C90E | Sodium Coco sulphate | 8.50 |
| BASF | DEHYTON MC | Sodium Cocoamphoacetate | 8.50 |
| UNIPEX | AMISOFT HS11P | Sodium Stearoyl Glutamate | 1.00 |
| BRENNTAG | MANNITOL | Mannitol | 3.00 |
| EPHYLA SAS | Frametime CX | Bentonite & Xanthan gum & Citric acid | 5.50 |
| EPHYLA SAS | CHITOVEG | Chitosan | 0.25 |
| BALLU CHIMIE | AEC8G | Capryloyl Glycine | 0.40 |
| BRENNTAG | Salicylic acid | Salicylic acid | 0.20 |
| MLW | Benzyl Alcohol | Benzyl alcohol | 0.60 |
| BRENNTAG | Sodium Benzoate | Sodium Benzoate | 0.50 |
| HITEX | Composition according to the present disclosure KERANAT | 1% Miliacin; 1% Phospholipids; 0.2% Glycosylceramides/ceramides | 0.70 |
| EPHYLA SAS | Desert date oil | *Balanites roxburghii* seed oil | 2.00 |
| | Fragrance | Parfum | 0.40 |
| | WATER | Aqua | q.s. |

Throughout the description, including the claims, the ranges of values should be understood to include the limits, unless specified otherwise.

Throughout the description, including the claims, the expressions "including a" and "comprising a" should be understood to be synonymous with the expressions "including at least one" and "comprising at least one", respectively, unless specified otherwise.

What is claimed is:

1. A cosmetic, pharmaceutical or dietary composition, comprising:
   from 0.01% to 10% by weight miliacin, based on the total weight of said cosmetic, pharmaceutical or dietary composition; and
   from 0.01% to 5% by weight of at least one sphingolipid, based on the total weight of said cosmetic, pharmaceutical or dietary composition; and optionally
   from 0.01% to 5% of at least one phospholipid, based on the total weight of said cosmetic, pharmaceutical or dietary composition; and
   a pharmaceutically acceptable medium or excipient, a dietetically acceptable medium, or a cosmetically acceptable medium.

2. The composition according to claim 1, wherein said at least one sphingolipid comprises at least one ceramide, at least one glycosylceramide, or a mixture thereof.

3. The composition according to claim 1, comprising from 0.1% to 1.0% by weight of said at least one sphingolipid.

4. The composition according to claim 2, comprising from 0.1% to 1% by weight of said at least one ceramide, said at least one glycosylceramide, or a mixture thereof.

5. The composition according to claim 1, comprising from 0.3% to 1.5% of said phospholipid.

6. The composition according to claim 1, comprising from 0.5% to 1.5% of said phospholipid.

7. The composition according to claim 1, comprising from 0.3% to 1.5% of said phospholipid.

8. The composition according to claim 1, comprising from 0.1% to 2% by weight of said miliacin.

9. A cosmetic, pharmaceutical or dietary composition, comprising:
   from 0.01% to 10% by weight miliacin, based on the total weight of said cosmetic or dietary composition;
   a polar organic solvent extract of wheat, wherein said polar organic solvent extract of wheat comprises a sphingolipid; and pharmaceutically acceptable medium or excipient, a dietetically acceptable medium or a cosmetically acceptable medium;
   said sphingolipid being present in said cosmetic, pharmaceutical or dietary composition in an amount of between 0.01% and 5% by weight, based on the total weight of said cosmetic, pharmaceutical or dietary composition.

10. A method for preparing the composition according to claim 1, comprising:
    a) obtaining a millet oil comprising miliacin,
    b) obtaining a polar organic solvent extract of wheat, wherein said polar organic solvent extract of wheat comprises a sphingolipid, and
    c) mixing the millet oil and the polar organic solvent extract of wheat.

11. The method of claim 10, wherein said obtaining a millet oil comprises extraction of millet seeds with a solvent selected from the group consisting of:
    supercritical $CO_2$;
    supercritical propane;
    hexane;
    ethanol; and
    isopropanol.

12. The method of claim 10, wherein said obtaining a polar organic solvent extract of wheat comprises extraction of wheat with ethanol.

13. The method of claim 10, wherein said mixing comprises mixing said millet oil and said polar organic solvent extract of wheat after each obtaining step.

14. The method of claim 11, wherein said mixing comprises injecting said polar organic solvent extract of wheat into a millet oil extraction circuit during extraction of millet seeds.

15. The method of claim 11, wherein said mixing comprises injecting said polar organic solvent extract of wheat into a millet oil extraction circuit during extraction of millet seeds with supercritical $CO_2$.

16. The method of claim 14, wherein said mixing comprises injecting said polar organic solvent extract of wheat into a millet oil extraction circuit during extraction of millet seeds with an oxygen-free, supercritical medium.

17. The method of claim 14, wherein said millet oil comprises:
   from 85% to 99% triglycerides;
   from 0.5% to 2% sterols;
   from 0.1% to 2% miliacin.

18. A method of reducing hair loss in a female patient in need thereof, comprising:
   administering an effective amount of a composition according to claim 1 to said female patient.

19. The method of claim 18, wherein said administering comprises orally administering said effective amount of said composition to said female patient; or
   topically administering said effective amount of said composition to said female patient.

20. A cosmetic, pharmaceutical or dietary composition, comprising:
   a combination of miliacin and a sphingolipid
   wherein the composition comprises from 20% to 80% by weight miliacin, based on the based on the combined weight of said combination of miliacin and a sphingolipid; and
   a pharmaceutically acceptable medium or excipient, a dietetically acceptable medium, or a cosmetically acceptable medium.

21. The composition of claim 1, said medium or excipient comprises millet oil.

22. The composition of claim 20, wherein said medium or excipient comprises millet oil.

23. The composition of claim 20, further comprising a phospholipid.

* * * * *